United States Patent [19]

Consaga et al.

[11] Patent Number: 5,114,506
[45] Date of Patent: May 19, 1992

[54] ENERGETIC COMPOSITES OF CYCLODEXTRIN NITRATE ESTERS AND NITRATE ESTER PLASTICIZERS

[75] Inventors: John P. Consaga, LaPlata; Steven L. Collignon, Waldorf, both of Md.

[73] Assignee: The United States of America as represented by the Secretary of the Navy, Washington, D.C.

[21] Appl. No.: 728,918

[22] Filed: Jul. 8, 1991

[51] Int. Cl.$^5$ .............................................. C06B 25/00
[52] U.S. Cl. ...................................... 149/88; 149/108
[58] Field of Search .................................. 149/88, 108

[56] References Cited

U.S. PATENT DOCUMENTS

| | | | |
|---|---|---|---|
| 1,836,568 | 12/1931 | Wrightsman | 149/108 |
| 3,300,348 | 1/1967 | Griffith | 149/88 |
| 3,399,089 | 8/1968 | Griffith | 149/108 |
| 4,014,719 | 3/1977 | Walls | 149/108 |

Primary Examiner—Edward A. Miller
Attorney, Agent, or Firm—Kenneth E. Walden; Roger D. Johnson

[57] ABSTRACT

An energetic composite made of a mixture of
(1) a solid nitrate ester of a cyclodextrin or a mixture of cyclodextrins; and
(2) an energetic organic nitrate ester plasticizer.

12 Claims, No Drawings

ENERGETIC COMPOSITES OF CYCLODEXTRIN NITRATE ESTERS AND NITRATE ESTER PLASTICIZERS

BACKGROUND OF THE INVENTION

This invention relates to energetic materials and more particularly to organic nitrate esters.

Many gun propellants and explosive composites are based on nitrocellulose. It would be desirable to provide relatively inexpensive energetic gun propellant or explosive composites which would have greater energy, greater thermal stability, and lower sensitivity to impact than comparable nitrocellulose based composites.

SUMMARY OF THE INVENTION

Accordingly an object of this invention is to provide new energetic composites.

Another object of this invention is to provide new energetic composites for producing improved gun propellants and explosives.

A further object of this invention is to provide new energetic composites that can be used to produce new gun propellants and explosives that are more thermally stable and less sensitive to impact and yet have greater energy than similar nitrocellulose based gun propellants and explosives.

These and other objects of this invention are accomplished by providing an energetic composite made of a mixture of (1) a solid nitrate ester of a cyclodextrin or mixture of cyclodextrins; and (2) an energetic organic nitrate ester plasticizer.

The energetic composite is useful in gun propellants or explosives.

DETAILED DESCRIPTION OF THE PREFERRED EMBODIMENT

The composites of this invention are mixtures of (1) a cyclodextrin nitrate ester or a mixture of cyclodextrin nitrate esters and (2) an energetic organic nitrate ester plasticizer. The cyclodextrin nitrate esters are useful as replacements for nitrocellulose (NC) in that they are more thermally stable and less sensitive to impact and yet have comparable or greater energy content than nitrocellulose. However, the cyclodextrin nitrate esters are dry powders that are sensitive to electrostatic discharge (EDS). For example, a β-cyclodextrin nitrate ester (β-CDN) ($C_{42}H_{52}N_{18}O_{71}$) has an ESD value of only 0.0125 joules. However, when 1,1,1-trimethylolethane trinitrate (TMETN) (ESD value 12.5 joules) is mixed with the β-cyclodextrin nitrate ester in a 2:1 weight ratio, the resulting composite mixture has a a waxy consistency and a ESD value of 12.5 joules (see Table 1). Note that the β-cyclodextrin nitrate ester has a low impact sensitivity (card gap of 0) and TMETN is more sensitive (card gap of 15-20). The 2:1 composite mixture also has a low impact sensitivity (card gap of 0) even though TMETN is the major component by weight. (See Table 1).

TABLE 1

| | 5 kg Impact (mm) | Sliding Friction, (lbs) | ESD (Joules) | Card Gap (Cards) | Cap Test |
|---|---|---|---|---|---|
| TMETN | ≧600 | ≧980 | ≧12.5 | 15-20 | #6 Test |
| β-CDN | ≧600 | ≧980 | 0.0125 | 0 | Negative |
| 2TMETN/ | ≧600 | ≧980 | ≧12.5 | 0 | |

TABLE 1-continued

| | 5 kg Impact (mm) | Sliding Friction, (lbs) | ESD (Joules) | Card Gap (Cards) | Cap Test |
|---|---|---|---|---|---|
| 1CDN | | | | | |

The cyclodextrin starting materials have cyclic structures consisting of 1,4-α-glucosidically linked D-glucose units. Preferred starting materials are α-cyclodextrin with six, β-cyclodextrin with seven or γ-cyclodextrin with eight glucosidically linked D-glucose units, or mixtures of these compounds. Most preferred is β-cyclodextrin.

Each D-glucose unit in a cyclodextrin compound has three free —OH groups capable of being nitrated to a nitrate ester group —$ONO_2$. Preferably an average of from 2 to 3, more preferably from 2.5 to 3, and still more preferably from 2.6 to 3 nitrate ester groups (—$ONO_2$) per D-glucose unit are present in the nitration product cyclodextrin nitrate ester. These ranges for nitrate ester content apply to all cyclodextrin nitrate esters including α-cyclodextrin nitrate esters, -cyclodextrin nitrate esters, γ-cyclodextrin nitrate esters, taken alone or as various mixtures thereof. Note that different α-cyclodextrin nitrate esters are based on the same basic α-cyclodextrin moiety and differ from each other only in the degree of nitration (nitrate ester unit content). The same is true of the β-cyclodextrin nitrate esters and also of the γ-cyclodextrin nitrate esters.

The cyclodextrins can be nitrated using conventional techniques that are used in the preparation of nitrocellulose. The degree of nitration can be controlled by varying the nitration conditions. From 70 to 90 percent nitric acid ($HNO_3$) may be used, though 90 percent $HNO_3$ (see Example 1) is preferred to achieve greater nitration. The nitration may also be accomplished by using 90% $HNO_3$ and sulfuric acid ($H_2SO_4$) (see Example 2) or 90% $HNO_3$ and oleum (see Example 3). In each of these methods care is taken to keep the reaction temperature below 30° C. during the nitration. Other methods that should work as well include (1) nitric acid and phosphoric acid, (2) nitric and acetic anhydride, (3) sodium nitrite and sulfuric acid, and (4) non-acidic conditions using nitronium tetrafluoroborate.

Preferred energetic organic nitrate ester plasticizers include 1,1,1-trimethylolethane trinitate (TMETN), 1,2,4-butanetriol trinitrate (BTTN), triethylene glycol dinitrate (TEGDN), nitroglycerin (NG),1,2-propyleneglycol dinitrate (PGDN), pentaerythritol trinitrate (PETRIN), diethylene glycol dinitrate (DEGN), or mixture thereof. More preferred energetic organic nitrate ester plasticizers include1,1,1-trimethylolethane trinitrate, 1,2,4-butanetriol trinitrate, triethylene glycol dinitrate, nitroglycerin, or mixtures thereof. Most preferred is 1,1,1-trimethylolethane trinitrate.

The exact operable range for the ratio of energetic organic nitrate ester plasticizer to cyclodextrin nitrate ester may vary with the choice of energetic nitrate ester plasticizer and cyclodextrin nitrate ester. At least enough plasticizer is used to convert a powdery cyclodextrin nitrate ester to a pliable or flexible (waxy or rubbery) composite. When this is done the electrostatic sensitivity (ESD) of the cyclodextrin nitrate ester is decreased to about that of the plasticizer while the impact sensitivity remains about as low as the cyclodextrin nitrate ester. As more plasticizer is added, a point is reached where the composite is saturated with plasticizer; plasticizer added beyond this point remains separate (neat) from the composite. As a result the impact sensitivity increases to that of the energetic organic nitrate ester plasticizer. Example 4 demonstrates this procedure using weight ratios of 1,1,1-trimethylolethane trinitrate (TMETN) to a β-cyclodextrin nitrate ester (with an average of about 2.6 nitrate esters per D-sucrose unit) of from 2:1 to 6:1.

A preferred embodiment of this invention is an energetic composite comprising (1) a nitrate ester of β-cyclodextrin which has an average of from 2.5 to 2.7 nitrate ester groups per D-glucose unit and (2) 1,1,1-trimethylolethane trinitate wherein the weight ratios of 1,1,1-trimethylolethane trinitate to the nitrate ester of β-cyclodextrin is preferably from about 2:1 to less than 6:1, and more preferably from 2:1 to 5:1.

A wide variety of polymers may be used as binders for this cyclodextrin nitrate ester/energetic organic nitrate ester plasticizer composites of this invention. These polymers generically have the desired properties of processibility and utility in propellants or explosives generally have a molecular weight of less than 10,000, and a viscosity of between about 20 and about 500 poise. Suitable polymers include: epoxy terminated polybutadiene, carboxyl terminated polybutadiene, hydroxyl terminated polybutadiene, mercaptyl terminated polybutadiene, episulfide terminated polybutadiene, epoxy terminated polyether, carboxyl terminated polyether, hydroxyl terminated polyether, mercaptyl terminated polyether, episulfide terminated polyether, hydroxy terminated (e.g., DURACARB), polycaprolactones, and liquid copolymer systems such as polybutadiene-styrene and polybutadiene-acrylonitrile having functional groups which include, epoxy terminal groups, carboxyl terminal groups, hydroxyl terminatal groups, mercaptyl terminal groups and episulfide terminal groups.

Example 5 illustrate this procedure using an isocyanate terminated R45M polymer to form a flexible gum stock from a 2:1 weight ratio complex of TMETN plasticier/β-cyclodextrin nitrate ester complex.

The general nature of the invention having been set forth, the following examples are presented as specific illustrations thereof. It will be understood that the invention is not limited to these specific examples, but is susceptible to various modifications that will be recognized by one of ordinary skill in the art.

EXAMPLE 1

From β-Cyclodextrin and 90% $HNO_3$

β-cyclodextrin (200 grams) was added to 1296 grams of 90% $HNO_3$ over a 15 minute period while the reaction temperature was kept at 30° C. or less. The reaction solution was then cooled to 0° C. and then several liters of water was added slowly with stirring causing the β-cyclodextrin nitrate ester to precipitate. The product β-cyclodextrin nitrate ester precipitate was filtered out and washed with water until the pH of the wash water wash 6.0–7.0. The product β-cyclodextrin nitrate ester was then dried under heat and vacuum.

EXAMPLE 2

From β-Cyclodextrin, 90% $HNO_3$, and Oleum

β-cyclodextrin (50 g) was added slowly to a stirred 90% $HNO_3$ acid solution (291 g) while the temperature was maintained at 30° C. or just below. Oleum (480 g) was then added slowly to the stirred solution while the temperature was maintained at 30° C. or just below. The product β-cyclodextrin nitrate ester stayed in solution, but precipitated on the addition of more oleum. The product β-cyclodextrin nitrate ester was then filtered out and washed with water until the pH of the wash water was 6.0–7.0. The β-cyclodextrin nitrate ester was then dried under heat (85° C.) and vacuum.

EXAMPLE 3

From β-Cyclodextrin, 90% $HNO_3$, and $H_2SO_4$

β-cyclodextrin (750 g) was added to a stirred solution of 2650 g of 90% $HNO_3$ and 556 g of $H_2SO_4$ while the temperature of the solution was kept at or just below 30° C. After a 2 to 3 hour reaction time water was added slowly to precipitate the product β-cyclodextrin nitrate ester. The precipitated β-cyclodextrin nitrate ester was filtered out and washed with water until the pH of the wash water was 6.0–7.0. The product β-cyclodextrin nitrate ester was then dried under heat (85° C.) and vacuum. β-cyclodextrin (seven D-glucose units) with 18 of its 21 active hydroxy (—OH) being nitrated to nitrate ester groups (—$ONO_2$) would have an empirical formula of $C_{42}H_2O_{71}N_{18}$ and a calculated molecular weight (M.W.) of 1945. Found M.W 1989. Calculated for $C_{42}H_2O_{71}N_{18}$: C, 25.93; H, 2.70; N, 12.96. Found from mixed acid Galbraith analysis: C, 25.83; H, 2.86; N, 11.86.

EXAMPLE 4

Forming TMETN/β-Cyclodextrin Nitrate Ester Complexes

β-cyclodextrin nitrate ester (2.5 g) prepared according to example 3 was dissolved in acetone and mixed with 5 g of 1,1,1-trimethylolethane trinitrate (TMETN) (stabilized with 1% 2NDPA). The solution was left overnight at ambient conditions. Then the acetone was removed slowly. The product 2TMETN/1CDN complex was a thick waxy material having a card gap test score of 0. The process was repeated for complexes having weight rations of TMETN to β-cyclodextrin nitrate ester of 3:1, 4:1, 5:1, and 6:1. All these composites were thick waxy materials. These materials were tested and the results are summarized in Table 2.

TABLE 2

| | 5 kg Impact mm | Sliding Fiction lb | ESD Joules | DTA(Onset/ Exotherm) | Card Gap |
|---|---|---|---|---|---|
| 2TMETN/ 1CDN Propellant | ≥600 | ≥980 | ≥12.5 | 140° C./178° C. | 0 |
| 4TMETN/ 1CDN Propellant | ≥600 | ≥980 | ≥12.5 | 140° C./178° C. | 0 |
| 5TMETN/ 1CDN Propellant | ≥600 | ≥980 | ≥12.5 | 140° C./178° C. | 0 |
| 6TMETN/ 1CDN Propellant | 225 | ≥980 | ≥12.5 | 110° C./172° C. | 0 |

Based on the data the 5/1 ratio was selected for scale-up to a 1-gallon propellant mix. The 6/1 ratio lost impact and had a lower onset in the DTA, which is consistent with non-complexed (neat) TMETN.

EXAMPLE 5

The 2TMETN/1CDN complex (14.06 g) produced according to example 4 was mixed with isocyanate terminated R45M (0.70 g) and degassed at 40° C. in vacuum. The gumstock was cured in a 50° C. over for 1 day. The resulting gumstock was flexible.

Obviously, numerous modifications and variations of the present invention are possible in light of the foregoing teachings. It is therefore to be understood that within the scope of the appended claims the invention may be practiced otherwise than as specifically described herein.

What is claimed and desired to be secured by Letters Patent of the United States is:

1. An energetic composite comprising a mixture of:
   A. an energetic organic solid material that is a nitrate ester of a cyclodextrin or a mixture of cyclodextrins which has an average of from 2 to 3 nitrate ester groups per D-glucose unit in the cyclodextrin or cyclodextrin mixture; and
   B an energetic nitrate ester plasticizer;
   wherein the amount of the plasticizer ranges from the amount required to produce a flexible composite up to the amount that saturates the composite.

2. The energetic composite of claim 1 wherein the nitrate ester of the cyclodextrin or mixture or cyclodextrins has an average of from 2.5 to 3 nitrate ester groups per D-glucose unit in the cyclodextrin or cyclodextrin mixture.

3. The energetic composite of claim 2 wherein the nitrate ester of the cyclodextrin or the mixture of cyclodextrins has an average of 2.6 to 3 nitrate ester groups per D-glucose unit in the cyclodextrin or cyclodextrin mixture.

4. The energetic composite of claim 1 wherein the energetic solid material (A) is a nitrate ester of α-cyclodextrin, β-cyclodextrin, γ-cyclodextrin, or mixtures thereof.

5. The energetic composite of claim 4 wherein the energetic solid material is a nitrate ester of α-cyclodextrin.

6. The energetic composite of claim 4 wherein the energetic solid material is a nitrate ester of β-cyclodextrin.

7. The energetic composite of claim 4 wherein the energetic solid material is a nitrate ester of γ-cyclodextrin.

8. The energetic composite of claim 1 wherein the energetic organic nitrate ester is 1,1,1-trimethylolethane trinitrate, 1,2,4-butanetriol trinitrate, triethylene glycol dinitrate, nitroglycerin, 1,2-propyleneglycol dinitrate, pentaerythritol trinitrate, diethylene glycol dinitrate or mixture thereof.

9. The energetic composite of claim 8 wherein the energetic organic nitrate ester is 1,1,1-trimethylolethane trinitrate, 1,2,4-butanetriol trinitrate, triethylene glycol dinitrate, nitroglycerin, or mixture thereof.

10. The energetic composite of claim 9 wherein the energetic nitrate ester is 1,1,1-trimethylolethane trinitrate.

11. An energetic composite comprising a mixture of:
    A. a nitrate ester of β-cyclodextrin which has an average of from 2.5 to 2.7 nitrate ester groups per D-glucose unit; and
    B. 1,1,1-trimethylolethane trinitrate as a plasticizer;
    wherein the weight ratio of 1,1,1-trimethylolethane trinitrate to the nitrate ester of β-cyclodextrin is from about 2:1 to less than 6:1.

12. The energetic composite of claim 11 wherein the weight ratio of 1,1,1-trimethylolethane trinitrate to the nitrate ester of β-cyclodextrin is from 2:1 to 5:1.

* * * * *